United States Patent [19]
Dash et al.

[11] Patent Number: 4,848,322
[45] Date of Patent: Jul. 18, 1989

[54] ENDOSCOPY SHIELD

[76] Inventors: Georgia P. Dash, 7805 Lafayette Ave., Melrose Park, Pa. 19126; Dorothy L. Borton, 503 Rodman Ave., Jenkintown, Pa. 19046

[21] Appl. No.: 145,531
[22] Filed: Jan. 19, 1988
[51] Int. Cl.$^4$ ............................................. A61B 1/00
[52] U.S. Cl. ........................................ 128/4; 128/857
[58] Field of Search ................... 128/132 R, 132 D, 3, 128/4, 5, 6, 7, 303.15, 303 R, 356, 857

[56] References Cited

U.S. PATENT DOCUMENTS

| | | | |
|---|---|---|---|
| 1,679,950 | 8/1928 | Stern | 128/303.15 |
| 3,144,020 | 8/1964 | Zingale | 128/4 |
| 3,370,302 | 2/1968 | Karlyn | 128/132 R X |
| 3,522,800 | 8/1970 | Lesser | 128/132 R X |
| 4,022,194 | 5/1977 | Banez | 128/4 |
| 4,593,681 | 6/1986 | Soni | 128/4 |
| 4,616,641 | 10/1986 | Teeple | 128/132 R |
| 4,633,869 | 1/1987 | Schmieding | 128/303 R |
| 4,657,020 | 4/1987 | Lifton | 128/356 |

Primary Examiner—William H. Grieb
Attorney, Agent, or Firm—Ratner & Prestia

[57] ABSTRACT

A shield for use with endoscopes has a flexible rim for adjustably conforming the shield to a concave shape to form a protected region for the face of an endoscope user. The shield is provided with a hole for sealingly receiving an endoscope. The seal between the endoscope and the shield is maintained when the endoscope is moved to different angles with respect to the shield.

20 Claims, 2 Drawing Sheets

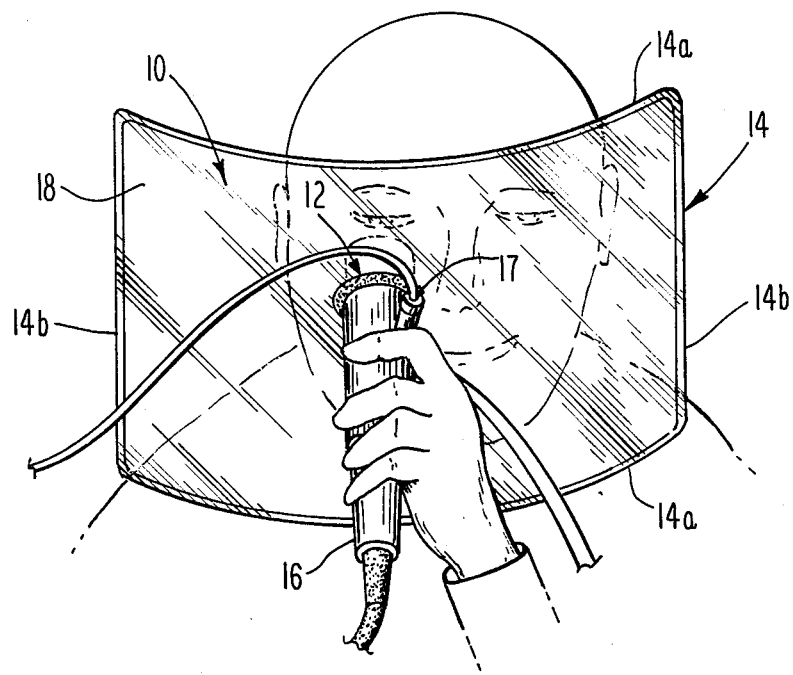
Fig. 1
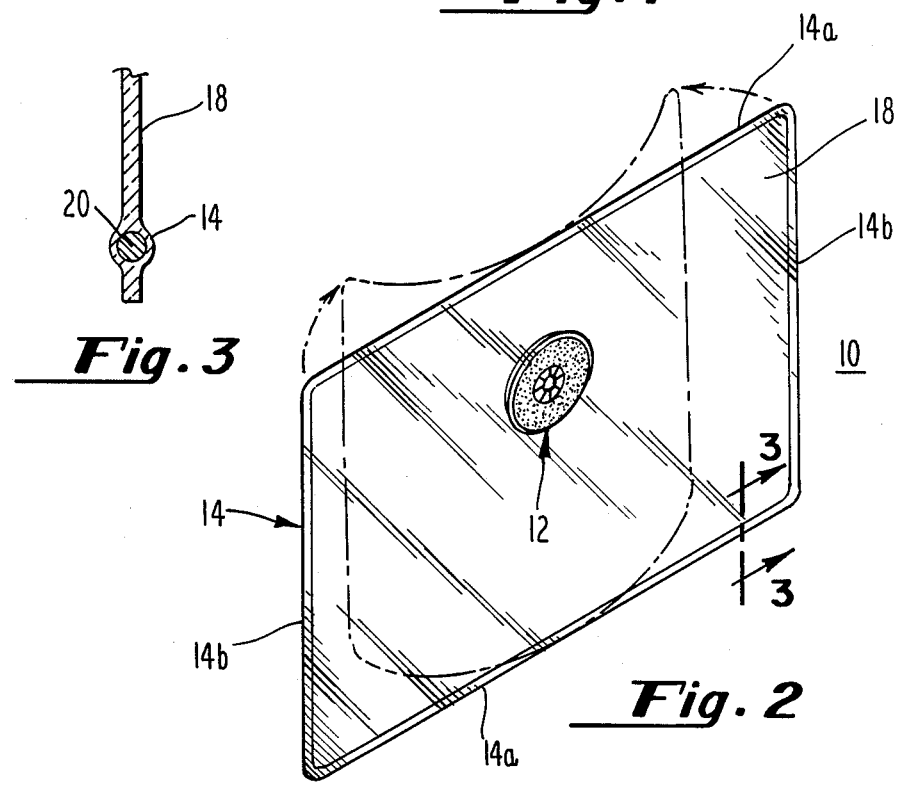
Fig. 3
Fig. 2

ENDOSCOPY SHIELD

BACKGROUND OF THE INVENTION

A. Field of the Invention

This invention relates, in general, to medical diagnostics and, in particular, to a shield for use with an endoscope to protect the user from body fluid splashback.

B. Background Art

In the examination of patients by physicians using endoscopes or similar equipment, blood or other body fluids are withdrawn from patients using, for example, a suction technique. Periodically, this examination process results in a splashback of blood or body fluid which may come into contact with the skin of the scope user. If the patient under examination suffers from a contagious disease, the scope user is in danger of contracting the disease. This danger is particularly great if the user has a skin break or if the splashback of blood or body fluid comes in contact with a mucous membrane of the user.

Even though these examinations are not surgical procedures, to guard against splashback contamination which may cause the spread of a contagious disease, scope users sometimes wear gloves, a surgical cap and a mask as well as goggles to cover their eyes. This regimen has a number of drawbacks. Users who wear glasses encounter difficulty in wearing goggles over the glasses. Additionally, the wearing of goggles interferes with the users' accurate use of the scope eyepiece Under some conditions, the goggles become clouded with condensation. Also, portions of the upper cheek, neck and ears of the scope user still remain exposed to potential splashbacks in spite of using the uncomfortable and restrictive cap, mask and goggles.

A rigid shield and instrument holder to protect a scope user during use of a fiber optic scope is shown in U.S. Pat. No. 4,022,194 issued to Banez. The shield of Banez is intended to block and catch in a trowel fluids which splash from a patient during use of the fiber optic scope. However, this shield is rigidly secured to the scope and its use is very restrictive. Furthermore, the shield of Banez does not entirely protect the user's face.

Another medical shield is taught in U.S. Pat. No. 1,679,950 issued to Stern. The shield of Stern is adapted to fit onto an apparatus for surgical resection, and is not adapted to protect the face, neck, and ears of a user. Likewise, a shield for a resectoscope sheath disclosed in U.S. Pat. No. 3,144,020 issued to Zingale, a latex rubber protector designed for an endoscope taught in U S. Pat. No. 4,657,020 issued to Lifton and a pad for a surgical instrument taught in U.S. Pat. No. 4,633,869 issued to Schmieding are all ineffective in protecting adequately the face, neck and ears of a user of an endoscope from contact with splashed fluids during endoscopic examination.

SUMMARY OF THE INVENTION

A shield for use with endoscope has a flexible rim for adjustably conforming the shield to a concave shape to form a protected region for the face of an endoscope user. The vertical dimension of the shield is sufficient to extend the length of the user's face and the horizontal dimension is sufficient to cover the sides of the face of the user. The shield is provided with a hole for sealingly receiving an endoscope.

BRIEF DESCRIPTION OF THE DRAWINGS

FIG. 1 is a perspective view of the endoscopy shield of the present invention mounted on an endoscope for use by an endoscope user;

FIG. 2 is a perspective view of the endoscopy shield of FIG. 1;

FIG. 3 is a partial cross-sectional view of the shield of FIG. 2 taken along line 3—3 of FIG. 2;

DETAILED DESCRIPTION OF THE INVENTION

Figure 4:
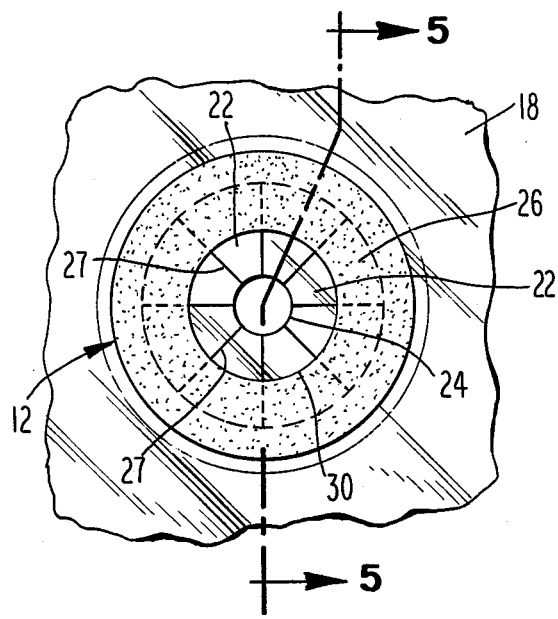
FIG. 4 is a close up of an opening in the shield of FIG. 1 adapted to receive the eyepiece of an endoscope.

Referring now to FIGS. 1-3, there is shown endoscope shield 10 of the present invention. Endoscope shield 10 includes flexible clear plastic sheet 18 which is seam free to prevent passage of body fluids while permitting an endoscope user an unrestricted and undistorted view through clear plastic sheet 18. Shield 10 is sealingly mounted on fiber optic endoscope 16 by way of opening 12 and protects the face, neck and ears of a user from splashback during use of endoscope 16. Shield 10 may be positioned from about one inch to about two inches from the front of the face of a user when shield 10 is thus mounted on endoscope 16 and the user looks into the eyepiece of endoscope 16.

Clear plastic sheet 18 is provided with flexible outer rim portion 14 around the entire perimeter of clear plastic sheet 18 to permit a user of endoscope shield 10 to adjust the shape of shield 10, for example, to a concave shape in which shield 10 is partially wrapped around the face of the user while the user is looking into endoscope 16. When bent, flexible outer rim portion 14 maintains its bent shape thereby retaining shield 10 in a wrapped around position as adjusted by the user. For the embodiment of the invention illustrated, flexible outer rim portion 14 includes a malleable wire 20 embedded in plastic sheet 18. However, other means, such as a malleable metal on the surface of sheet 18, can be used for providing flexible shaping of sheet 18 and retaining sheet 18 in an adjusted position. Furthermore, the malleable material does not have to be at the edge of clear plastic sheet 18 to provide flexible shaping of sheet 18. Preferably flexible outer rim portion 14 is bent to maintain clear plastic sheet 18 from about one inch to about two inches from the sides of the face of a user.

It will be understood that it is most important to protect all of the mucous membrane of a user from contact with splashback because many disease causing bacteria and viruses can rapidly cross over mucous membrane and enter the blood stream of the user. Membranes of this type are found in the mouth, nose and eyes. It is desirable to further protect a user as much as is practical including the neck and the front of the face up to the hair line as well as the sides of the face and ears.

Thus upper and lower horizontal edges 14a of flexible outer rim portion 14 are bent to permit endoscope shield 10 to be shaped to protect the lateral aspects of the user's neck and face and to substantially protect the user's ears. It is preferred that the ears of a user be at least partially protected by bent shield 10 and it is more preferred that the ears be completely protected. The lateral aspects of the user's neck and face are understood to comprise the sides of the user's neck and face.

The horizontal dimension of shield 10, understood to include the arc length of horizontal edges 14a of flexible outer rim portion 14, is sufficient to permit vertical edges 14b of shield 10 to extend to a wrapped around position wherein the lateral aspects of the face and neck of a user are protected while the user is looking into endoscope 16. However, the horizontal dimension of shield 10 can be increased to further extend to a wrapped around position wherein the ears of a user are substantially protected. The vertical dimension of shield 10, understood to include the arc length of vertical edges 14b, should be sufficient to protect the user from the neck to the hairline.

A horizontal dimension of approximately thirteen and one-half inches formed to have an arc of approximately one hundred eight degrees and a vertical dimension of approximately ten and one-half inches are sufficient to achieve these goals and protect the average person. However, it will be understood that dimensions greater or smaller than these may be used to achieve the desired shielding provided the dimensions are large enough to protect the user of the endoscope from contact with splashback of blood or other body fluid as described.

Because flexible outer rim portion 14 of clear plastic sheet 18 is provided around the entire periphery of clear plastic sheet 18, the shape of both the vertical side edges 14b of outer rim portion 14 and the upper and lower horizontal edges 14a of outer rim portion 14 can be adjusted, although FIGS. 1 and 3 only show bending of the horizontal edges. This permits endoscope shield 10 to be shaped to a configuration desired by the user in which shield 10 does not interfere with the use of components of endoscope 16, while providing optimum protection to the user.

Splashback during use of endoscope 16 may, for example, be discharged from a patient or from aspiration port or biopsy forceps opening 17 of endoscope 16. Thus when suction is to be performed or a tissue sample is to be obtained by way of port 17, shield 10 may be bent out of the way to provide room to work near port 17. The volume of this splashback may be from a few milliliters to thirty milliliters or more.

Figure 5:
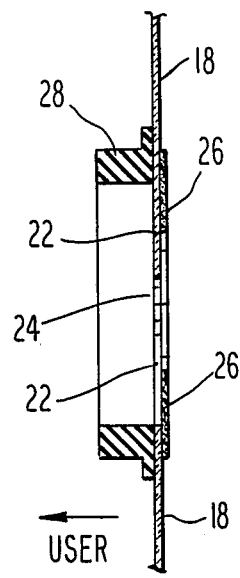
FIG. 5 is a cross-sectional view of the opening of FIG. 4 taken along 5—5 of FIG. 4.
Figure 6:
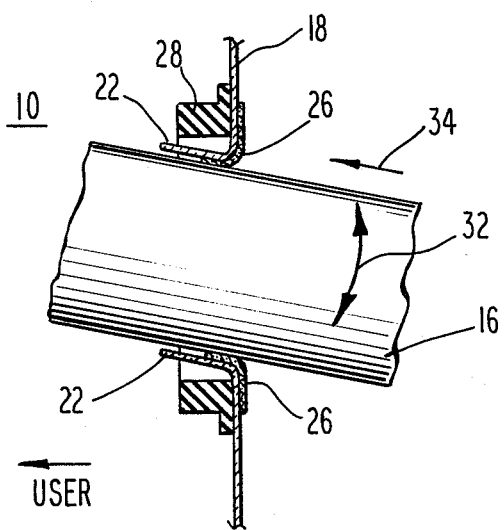
FIG. 6 is a cross-sectional view of the opening of FIG. 4 with a portion of an endoscope extending through the opening.

Referring now to FIGS. 4, 5, and 6, there is shown a more detailed representation of opening 12 through which the tubular eyepiece of endoscope 16 extends and the means for mounting and retaining the shield on endoscope 16. A hole 24 is provided through clear plastic sheet 18 and forms the center of opening 12. A plurality of slits 27 extend radially from hole 24. Thus a plurality of flexible sections 22 are defined by slits 27.

A resilient membrane 26 having an opening 30 is adhered to clear plastic sheet 18 on the side of clear plastic sheet 18 away from the user of endoscope 16. Opening 30 of resilient membrane 26 is concentric with hole 24 and has a radius larger than the radius of hole 24. Slits 27 extend radially beyond the radius of opening 30. Resilient membrane 26 may be formed of latex.

Collar 28, also concentric with hole 24, is adhered to the user's side of clear plastic sheet 18, opposite the side of membrane 26. Collar 28 is slightly stretchable and may be formed of hard rubber, plastic or any other suitable material. Hard, stretchable collar 28 provides reinforcement for opening 12 and helps to stabilize shield 10 when shield 10 is mounted on endoscope 16.

The radius of stretchable collar 28 is selected such that a small amount of stretching or expanding of collar 28 permits a variety of sizes of endoscopes to pass through opening 12 when collar 28 is adhered to plastic sheet 18. Collar 28 also provides a grip for holding shield 10 when mounting shield 10 on endoscope 16 or removing shield 10 from endoscope 16.

When shield 10 is mounted on endoscope 16, flexible sections 22 yield in the direction of arrow 34 which indicates the direction of motion of endoscope 16 relative to shield 10. When flexible sections 22 yield they fold in the direction of arrow 34 towards the user side of sheet 18 and resiliently press back towards endoscope 16. Likewise, flexible membrane 26 expands and folds, yielding in the direction of arrow 34 toward the user side of sheet 18.

Opening 30 of resilient membrane 26 is chosen to be less than the smallest diameter endoscope to be used with the shield. Thus when endoscope 16 is inserted through opening 12, opening 30 of resilient membrane 26 stretchably closes upon and resiliently grasps the entire circumference of the tubular portion of endoscope 16 extending through opening 12. When opening 30 of resilient membrane 26 resiliently grasps the entire circumference of endoscope 16, resilient membrane 26 seals gaps between sheet 18 and endoscope 16 thereby tightly sealing shield 10 around endoscope 16. Thus fluids are prevented from passing between sheet 18 and endoscope 16 by way of opening 12 and the user is protected from fluids which may splatter on the opposite side of shield 10.

Thus shield 10 is effectively a one piece full-face screen with no gaps. While a particular embodiment of opening 12 is shown, it will be understood that shield 10 may be mounted on endoscope 16 by any type of opening which tightly seals shield 10 to endoscope 16 and permits no gaps through which fluids may pass. Furthermore, it will be understood that the embodiment of opening 12 as shown is particularly advantageous in that endoscope 16 may be moved without impediment from one angle with respect to shield 10 to another angle with respect to shield 10 as may be convenient during the use of endoscope 16, for example, as indicated by arrow 32, without losing the seal between endoscope 16 and shield 10. Furthermore, endoscope 16 and shield 10 may be rotated with respect to each other without losing the seal between endoscope 16 and shield 10.

Further, it will be understood that while shield 10 is described with respect to endoscope 16, shield 10 may be just as advantageously used with a gastroscope, colonoscope, sigmoidoscope or bronchoscope, as well as any device having a tubular eyepiece portion, when possible contagious splashback may occur.

Opening 12 may be located approximately half way across the horizontal length of clear plastic sheet 18 of shield 10. This positioning of opening 12 permits protection of both lateral aspects of the face of a user and preferably the ears of a user when opening 12 is positioned slightly to the left or the right of the mid-sagital line of the user in order to allow the user to view endoscope eyepiece 16 with either the left or right eye. Additionally, opening 12 should be above the mid-point of shield 10 in the vertical dimension to the extent that the eyes are above the mid-point between the bottom of the neck of a user and the hairline of a user.

We claim:

1. A shield for use with an endoscope or the like having a tubular eyepiece for protecting a user from splashback, comprising:
   a clear sheet having a vertical dimension sufficient to extend substantially along the entire length of the face of the user and having a horizontal dimension sufficient to extend to cover at least the lateral aspects of the face of the user;
   malleable material extending horizontally across said sheet for maintaining said sheet in an adjusted concave shape to form a protected region for the face of the user; and,
   means for sealingly mounting and retaining said sheet on said tubular eyepiece.

2. The shield of claim 1 further including malleable material extending vertically across said sheet.

3. The shield of claim 2 wherein said malleable material comprises lengths of metal wire embedded in said sheet.

4. The shield of claim 2 wherein said malleable material extends along the edges of said sheet.

5. The shield of claim 1 wherein said horizontal dimension is approximately 13.5 inches and said vertical dimension is approximately 10.5 inches.

6. The shield of claim 1 wherein the mounting and retaining means comprises adjustable sealing means for adjusting to receive plurality of sizes of tubular eyepieces and for sealingly closing around said tubular eyepieces.

7. The shield of claim 1 wherein the mounting and retaining means includes means for supporting the sheet at a plurality of angles with respect to the eyepiece portion while sealingly retaining the eyepiece portion.

8. The shield of claim 1 wherein the horizontal dimension is sufficient to extend to cover the ears of the user.

9. A shield for use with an endoscope or the like having a tubular eyepiece for protecting a user from splashback, comprising:
   a clear sheet having a vertical dimension sufficient to extend substantially along the entire length of the face and having a horizontal dimension sufficient to extend to cover at least the lateral aspects of the face of the user to protect from splashback; and
   means for mounting said sheet on said eyepiece at a plurality of angles with respect to said eyepiece while sealingly retaining said eyepiece.

10. The shield of claim 9 wherein the mounting and retaining means comprises adjustable sealing means for adjusting to receive plurality of sizes of tubular eyepieces and for sealingly closing around said tubular eyepieces.

11. A shield for use with an endoscope or the like having a tubular eyepiece for protecting a user from splashback, comprising:
   a clear sheet having a vertical dimension sufficient to extend substantially along the entire length of the face and having a horizontal dimension sufficient to extend to cover at least the lateral aspects of the face of the user to protect from splashback; and,
   means for sealingly mounting and retaining said sheet on a tubular eyepiece.

12. The shield of claim 11 wherein the mounting and retaining means comprises adjustable sealing means for adjusting to receive plurality of sizes of tubular eyepieces and for sealingly closing around said tubular eyepieces.

13. A shield for use with an endoscope or the like having a tubular eyepiece for protecting a user from splashback, comprising:
   a clear sheet having:
   (a) a vertical dimension sufficient to extend substantially along the entire length of the face of the user and a horizontal dimension sufficient to extend to cover at least the lateral aspects of the face of the user, and
   (b) a first hole and bendable sections around said first hole formed by slits in said sheet extending radially from said first hole for bendably adjusting the size of said first hole to receive tubular eyepieces of differing sizes;
   malleable material extending horizontally across said clear sheet for maintaining said sheet in an adjusted concave shape to form a protected region for the face of the user; and
   a flexible membrane having a second hole concentric with said first hole in said clear sheet and attached to said sheet for stretchably receiving and resilient grasping the entire circumference of a tubular eyepiece.

14. The shield of claim 13 further including a collar attached to said clear sheet concentric with said first hole in said sheet and said second hole in said flexible membrane and adapted to provide a grip for gripping said sheet to sealingly mount and retain said sheet on a tubular eyepiece.

15. A shield for use with an endoscope or the like having a tubular eyepiece for protecting a user from splashback, comprising:
   a clear sheet having a vertical dimension sufficient to extend substantially along the entire length of the face and having a horizontal dimension sufficient to extend to cover at least the lateral aspects of the face of the user to protect from splashback; and
   means for mounting said sheet on an eyepiece at a plurality of angles with respect to said eyepiece while sealingly retaining said eyepiece, said means including:
   (a) a first hole in said clear sheet,
   (b) bendable sections of said sheet around said first hole formed by slits in said sheet extending radially from said first hole for bendably adjusting the size of said first hole to receive tubular eyepieces of differing sizes, and
   (c) a flexible membrane having a second hole concentric with said first hole attached to said sheet for stretchably receiving and resiliently grasping the entire circumference of a tubular eyepiece.

16. The shield of claim 15 further including a collar attached to said clear sheet concentric with said first hole in said sheet and said second hole in said flexible membrane and adapted to provide a grip for gripping said sheet to sealingly mount and retain said sheet on a tubular eyepiece.

17. A shield for use with an endoscope or the like having a tubular eyepiece for protecting a user from splashback, comprising:
   a clear sheet having:
   (a) a vertical dimension sufficient to extend substantially along the entire length of the face of the user and a horizontal dimension sufficient to extends to cover at least the lateral aspects of the face of the user, and
   (b) a first hole and bendable sections around said first hole formed by slits in said sheet extending radially from said first hole for bendably adjusting the size of said first hole to receive tubular eyepieces of differing size; and a flexible membrane having a second hole concentric with said first hole in said clear sheet and attached to said sheet for stretchably receiving and resiliently grasping the entire circumference of a tubular eyepiece.

18. The shield of claim 17 further including a collar attached to said clear sheet concentric with said first hole in said sheet and said second hole in said flexible membrane and adapted to provide a grip for gripping said sheet to sealingly mount and retain said sheet on a tubular eyepiece.

19. A shield for use with an endoscope or the like having a tubular eyepiece for protecting a user from splashback, comprising:

a clear sheet having a vertical dimension sufficient to extend substantially along the entire length of the face of the user and having a horizontal dimension sufficient to extend to cover at least the lateral aspects of the face of the user;

malleable material extending along a selected length of the edge of said sheet for maintaining and sheet in an adjusted concave shape to form a protected region for the face of the user; and means for sealingly mounting and retaining said sheet on said tubular eyepiece.

20. A shield for use with an endoscope or the like having a tubular eyepiece for protecting a user form splashback, comprising:

a clear sheet having a vertical dimension sufficient to extend substantially along the entire length of the face of the user and having a horizontal dimension sufficient to extend to cover at least the lateral aspects of the face of the user;

malleable material extending across said sheet and having a horizontal extent for maintaining said sheet in an adjusted concave shape which wraps around the face of the user to shield the front and lateral aspects of the face of the user; and means for sealingly mounting said retaining said sheet on said tubular eyepiece.

* * * * *